(12) United States Patent
Von Oepen et al.

(10) Patent No.: US 7,993,303 B2
(45) Date of Patent: Aug. 9, 2011

(54) STIFFENING SUPPORT CATHETER AND METHODS FOR USING THE SAME

(75) Inventors: Randolf Von Oepen, Los Altos Hills, CA (US); Ian J. Clark, West Bloomfield, MI (US); Lorcan Coffey, Tubingen (DE); Thomas Rieth, Hirrlingen (DE); Richard Newhauser, Redwood City, CA (US); Travis Yribarren, Coarsegold, CA (US); Marc Gianotti, Portola Valley, CA (US); Bernhard Uihlein, Dettingen (DE)

(73) Assignee: Abbott Laboratories, Abbott Park, IL (US)

( * ) Notice: Subject to any disclaimer, the term of this patent is extended or adjusted under 35 U.S.C. 154(b) by 828 days.

(21) Appl. No.: 11/738,384

(22) Filed: Apr. 20, 2007

(65) Prior Publication Data
US 2008/0058722 A1 Mar. 6, 2008

Related U.S. Application Data

(60) Provisional application No. 60/793,781, filed on Apr. 21, 2006.

(51) Int. Cl.
*A61M 29/00* (2006.01)
(52) U.S. Cl. ......... 604/103.09; 604/164.02; 604/164.03; 604/166.01; 604/167.01; 604/170.03; 604/524; 604/164.01; 604/95.04
(58) Field of Classification Search ............. 604/164.01, 604/164.02, 164.03, 166.01, 167.01, 170.03, 604/524, 103.09, 282, 95.04
See application file for complete search history.

(56) References Cited

U.S. PATENT DOCUMENTS

| | | | | |
|---|---|---|---|---|
| 4,624,381 A * | 11/1986 | Friedrich | ............ | 220/7 |
| 4,832,681 A | 5/1989 | Lenck | | |
| 4,921,479 A | 5/1990 | Grayzel | | |
| 5,057,092 A * | 10/1991 | Webster, Jr. | ............ | 604/527 |
| 5,139,496 A | 8/1992 | Hed | | |
| 5,180,366 A | 1/1993 | Woods | | |
| 5,195,978 A | 3/1993 | Schiffer | | |

(Continued)

FOREIGN PATENT DOCUMENTS
EP 0 279 959 8/1988
(Continued)

OTHER PUBLICATIONS
U.S. Appl. No. 11/738,382, filed Apr. 20, 2007, Von Oepen.
(Continued)

*Primary Examiner* — Nicholas D Lucchesi
*Assistant Examiner* — Scott Medway
(74) *Attorney, Agent, or Firm* — Workman Nydegger; Jonathan D. Feuchtwang (57) ABSTRACT

A support catheter that can puncture a heart septum with a guidewire without buckling and that can access difficult to reach arteries such as carotid or renal arteries from the aorta under difficult circumstances is provided. The support catheter comprises a catheter body having a proximal end, a distal end, and an interior wall surface defining a first lumen extending from the proximal end toward the distal end. A second lumen is disposed between the interior wall surface and an outer surface of the catheter body. A plurality of stiffening members is disposed around the second lumen, the plurality of stiffening members being engageable to selectively stiffen the catheter body. In another configuration, the catheter further comprises a second plurality of stiffening members disposed between the first lumen and the second lumen.

26 Claims, 5 Drawing Sheets

U.S. PATENT DOCUMENTS

| | | | | |
|---|---|---|---|---|
| 5,250,069 | A * | 10/1993 | Nobuyoshi et al. | 606/192 |
| 5,320,605 | A | 6/1994 | Sahota | |
| 5,324,255 | A | 6/1994 | Passafaro et al. | |
| 5,378,237 | A | 1/1995 | Boussignac et al. | |
| 5,380,273 | A | 1/1995 | Dubrul et al. | |
| 5,385,563 | A | 1/1995 | Gross | |
| 5,405,380 | A * | 4/1995 | Gianotti et al. | 623/1.15 |
| 5,423,773 | A | 6/1995 | Jimenez | |
| 5,437,288 | A | 8/1995 | Schwartz et al. | |
| 5,443,454 | A | 8/1995 | Tanabe et al. | |
| 5,454,795 | A | 10/1995 | Samson | |
| 5,460,608 | A * | 10/1995 | Lodin et al. | 604/103.09 |
| 5,507,751 | A | 4/1996 | Goode et al. | |
| 5,647,846 | A | 7/1997 | Berg et al. | |
| 5,662,622 | A | 9/1997 | Gore et al. | |
| 5,702,439 | A | 12/1997 | Keith et al. | |
| 5,709,658 | A | 1/1998 | Sirhan et al. | |
| 5,720,735 | A | 2/1998 | Dorros | |
| 5,855,563 | A | 1/1999 | Kaplan et al. | |
| 5,906,606 | A | 5/1999 | Chee et al. | |
| 5,951,517 | A | 9/1999 | Lampropoulos et al. | |
| 6,017,324 | A | 1/2000 | Tu et al. | |
| 6,022,309 | A | 2/2000 | Celliers et al. | |
| 6,152,909 | A | 11/2000 | Bagaoisan et al. | |
| 6,210,393 | B1 | 4/2001 | Brisken | |
| 6,210,404 | B1 | 4/2001 | Shadduck | |
| 6,217,503 | B1 | 4/2001 | Weinberger et al. | |
| 6,221,100 | B1 * | 4/2001 | Strecker | 623/1.22 |
| 6,241,744 | B1 | 6/2001 | Imran et al. | |
| 6,261,273 | B1 | 7/2001 | Ruiz | |
| 6,299,595 | B1 | 10/2001 | Dutta et al. | |
| 6,327,505 | B1 | 12/2001 | Medhkour et al. | |
| 6,398,772 | B1 | 6/2002 | Bond et al. | |
| 6,398,791 | B1 | 6/2002 | Que et al. | |
| 6,416,740 | B1 | 7/2002 | Unger | |
| 6,440,161 | B1 | 8/2002 | Madrid et al. | |
| 6,461,383 | B1 | 10/2002 | Gesswein et al. | |
| 6,482,218 | B1 | 11/2002 | Tran | |
| 6,579,246 | B2 | 6/2003 | Jacobsen et al. | |
| 6,582,390 | B1 | 6/2003 | Sanderson | |
| 6,652,508 | B2 | 11/2003 | Griffin et al. | |
| 6,679,879 | B2 | 1/2004 | Shadduck | |
| 6,682,502 | B2 | 1/2004 | Bond et al. | |
| 6,790,170 | B2 | 9/2004 | Moody et al. | |
| 6,849,077 | B2 | 2/2005 | Ricci | |
| 6,869,416 | B2 | 3/2005 | Windheuser et al. | |
| 6,942,680 | B2 * | 9/2005 | Grayzel et al. | 606/194 |
| 6,962,604 | B2 * | 11/2005 | Hijlkema | 623/1.15 |
| 7,044,933 | B2 | 5/2006 | VanDiver et al. | |
| 7,329,223 | B1 | 2/2008 | Ainsworth et al. | |
| 7,344,528 | B1 | 3/2008 | Tu et al. | |
| 7,789,906 | B2 * | 9/2010 | Blank | 623/1.16 |
| 2001/0008976 | A1 | 7/2001 | Wang | |
| 2001/0031243 | A1 | 10/2001 | Unger | |
| 2002/0022831 | A1 | 2/2002 | O'Connor et al. | |
| 2002/0072710 | A1 * | 6/2002 | Stewart et al. | 604/164.02 |
| 2002/0107473 | A1 | 8/2002 | Bond et al. | |
| 2002/0123716 | A1 | 9/2002 | VanDiver et al. | |
| 2002/0123738 | A1 | 9/2002 | Jansen et al. | |
| 2003/0009157 | A1 | 1/2003 | Levine et al. | |
| 2003/0055377 | A1 | 3/2003 | Sirhan et al. | |
| 2003/0069522 | A1 | 4/2003 | Jacobsen et al. | |
| 2003/0135261 | A1 | 7/2003 | Kugler et al. | |
| 2003/0191449 | A1 | 10/2003 | Nash et al. | |
| 2004/0044350 | A1 | 3/2004 | Martin et al. | |
| 2004/0054322 | A1 | 3/2004 | Vargas | |
| 2004/0054347 | A1 | 3/2004 | Zadno-Azizi et al. | |
| 2004/0093044 | A1 | 5/2004 | Rychnovsky et al. | |
| 2004/0098021 | A1 * | 5/2004 | Laguna | 606/194 |
| 2004/0102821 | A1 | 5/2004 | Kawata et al. | |
| 2004/0103516 | A1 * | 6/2004 | Bolduc et al. | 29/446 |
| 2004/0220473 | A1 | 11/2004 | Lualdi | |
| 2004/0225278 | A1 | 11/2004 | Poole et al. | |
| 2004/0230204 | A1 | 11/2004 | Wortley et al. | |
| 2005/0004522 | A1 * | 1/2005 | Katoh et al. | 604/164.01 |
| 2005/0021004 | A1 | 1/2005 | Cully et al. | |
| 2005/0182371 | A1 | 8/2005 | Wagner et al. | |
| 2005/0209582 | A1 | 9/2005 | Quinn et al. | |
| 2006/0085023 | A1 * | 4/2006 | Davies et al. | 606/192 |
| 2006/0190022 | A1 | 8/2006 | Beyar et al. | |
| 2007/0060880 | A1 | 3/2007 | Gregorich et al. | |
| 2007/0250149 | A1 | 10/2007 | Von Oepen et al. | |
| 2007/0270779 | A1 | 11/2007 | Jacobs et al. | |
| 2007/0293821 | A1 | 12/2007 | Yribarren et al. | |
| 2007/0293846 | A1 | 12/2007 | Von Oepen et al. | |
| 2007/0299392 | A1 | 12/2007 | Beyar et al. | |
| 2008/0065014 | A1 | 3/2008 | Von Oepen et al. | |

FOREIGN PATENT DOCUMENTS

| | | |
|---|---|---|
| EP | 0 596 635 | 5/1994 |
| EP | 0 598 635 | 5/1994 |
| EP | 0 916 359 | 5/1999 |
| EP | 1 475 120 | 11/2004 |
| EP | 1 607 119 | 12/2005 |
| GB | 2 143 920 | 2/1985 |
| WO | WO 88/08727 | 11/1988 |
| WO | WO 93/06780 | 4/1993 |
| WO | WO 96/07448 | 3/1996 |
| WO | WO 96/39205 | 12/1996 |
| WO | WO 97/23158 | 7/1997 |
| WO | WO 97/39690 | 10/1997 |
| WO | WO 99/15070 | 4/1999 |
| WO | WO 99/17826 | 4/1999 |
| WO | WO 99/21600 | 5/1999 |
| WO | WO 99/64098 | 12/1999 |
| WO | WO 00/03756 | 1/2000 |
| WO | WO 01/03762 | 1/2001 |
| WO | WO 01/07101 | 2/2001 |
| WO | WO 03/057060 | 7/2003 |
| WO | WO 03/105671 | 12/2003 |
| WO | WO 2004/064891 | 8/2004 |
| WO | WO 2004/096338 | 11/2004 |
| WO | WO 2006/002199 | 1/2006 |
| WO | WO 2006/058434 | 6/2006 |
| WO | WO 2006/122243 | 11/2006 |
| WO | PCT/US2007/067237 | 4/2007 |
| WO | PCT/US2007/067238 | 4/2007 |
| WO | PCT/US2007/067239 | 4/2007 |
| WO | PCT/US2007/067240 | 4/2007 |
| WO | PCT/US2007/067242 | 4/2007 |
| WO | PCT/US2007/067243 | 4/2007 |
| WO | PCT/US2007/067244 | 4/2007 |
| WO | WO 2007/124495 | 11/2007 |
| WO | WO 2007/124496 | 11/2007 |
| WO | WO 2007/124497 | 11/2007 |
| WO | WO 2007/124499 | 11/2007 |
| WO | WO 2007/124500 | 11/2007 |
| WO | WO 2007/124501 | 11/2007 |
| WO | WO 2007/143288 | 12/2007 |

OTHER PUBLICATIONS

U.S. Appl. No. 11/738,378, filed Apr. 20, 2007, Von Oepen.
U.S. Appl. No. 11/738,372, filed Apr. 20, 2007, Yribarren.
U.S. Appl. No. 11/738,368, filed Apr. 20, 2007, Jacobs.
U.S. Appl. No. 11/738,386, filed Apr. 20, 2007, Von Oepen.
U.S. Appl. No. 11/738,386, Sep. 28, 2009, Office Action.
U.S. Appl. No. 11/738,372, May 12, 2010, Office Action.
U.S. Appl. No. 11/738,372, Jul. 26, 2010, Office Action.
U.S. Appl. No. 11/738,378, May 12, 2010, Office Action.
U.S. Appl. No. 11/738,378, Aug. 17, 2010, Office Action.
U.S. Appl. No. 11/738,372, Dec. 23, 2010, Notice of Allowance.
U.S. Appl. No. 11/738,378, Oct. 4, 2010, Advisory Action.
U.S. Appl. No. 11/738,378, Nov. 26, 2010, Office Action.
U.S. Appl. No. 60/793,781, filed Apr. 21, 2006, Von Oepen et al.
U.S. Appl. No. 11/738,382, Jan. 4, 2008, Office Action.
U.S. Appl. No. 11/738,382, Aug. 11, 2008, Office Action.
U.S. Appl. No. 11/738,382, Feb. 20, 2009, Office Action.
U.S. Appl. No. 11/738,382, Aug. 20, 2009, Office Action.
U.S. Appl. No. 11/738,372, Jun. 9, 2008, Office Action.
U.S. Appl. No. 11/738,372, Sep. 15, 2008, Office Action.

U.S. Appl. No. 11/738,372, Mar. 30, 2009, Office Action.
U.S. Appl. No. 11/738,372, Nov. 6, 2009, Office Action.
U.S. Appl. No. 11/738,382, Apr. 20, 2010, Office Action.
U.S. Appl. No. 11/738,386, Apr. 22, 2010, Office Action.
U.S. Appl. No. 11/738,368, Jan. 23, 2008, Office Action.
U.S. Appl. No. 11/738,368, Sep. 16, 2008, Office Action.
U.S. Appl. No. 11/738,368, Jan. 27, 2009, Office Action.
U.S. Appl. No. 11/738,368, Sep. 3, 2009, Office Action.
U.S. Appl. No. 11/738,378, Sep. 2, 2009, Office Action.

* cited by examiner

STIFFENING SUPPORT CATHETER AND METHODS FOR USING THE SAME

CROSS-REFERENCE TO RELATED APPLICATIONS

This application claims the benefit of the U.S. Provisional Patent Application No. 60/793,781, filed Apr. 21, 2006, and entitled "Medical Devices," which is incorporated herein by reference in its entirety. Further, this application is related to commonly-assigned U.S. patent application Ser. No. 11/738,386, entitled "Stiffening Support Catheters And Methods for Using The Same," filed on Apr. 20, 2007, which is incorporated herein by reference in its entirety.

BACKGROUND OF THE INVENTION

I. Field of the Invention

The present invention generally relates to the field of medical devices. More specifically, the present invention relates to support catheters or catheters that can be manipulated during deployment.

II. Related Technology

The use of intravascular devices to treat cardiovascular diseases is well known in the field of medicine. The need for a greater variety of devices to address different types of circumstances has grown tremendously as the techniques for using intravascular devices has progressed. One type of intravascular device is a catheter. Typically, an intravascular catheter is delivered into the body by first using a guide catheter that can be routed through the proper vessels in the body's vascular network in order to arrive at a site in need of a diagnostic or therapeutic technique.

Previously, support and guide catheters have been relatively simple and have been made of biocompatible plastics forming a shaft with a hollow internal lumen. The shaft is generally formed by one or more concentric tubes that are congruent to each other, where one tube typically provides support and the other tube(s) provide biocompatibility. Additionally, most guide catheters include a hub that is connected to a proximal end of the shaft in order to provide a mechanism for connecting another device, such as an inflation device or syringe. Usually, the tip of the support or guide catheter is flexible and/or shaped in order to allow for deployment and placement in the tortuous vasculature network.

In order for a medical professional to insert the catheter into the proper location in the vessel, longitudinal and rotational forces applied to the catheter must be translated to the distal end or the tip of the catheter. This enables the medical professional to maneuver the distal end of the catheter through various bends, junctions, or features of vessels in the vasculature. The tip of the catheter can be soft and flexible to prevent damage to the vasculature as the catheter is pushed or advanced therethrough. As such, the existing catheters are stiff enough to be advanced through a blood vessel, yet include the flexible tip to aid with directing the catheter through or around various bends or junctions.

There are problems, however, with the flexible distal sections used in the support catheters because too much flexibility may not allow for proper guidance of the catheters. Catheters having flexible distal ends have experienced increased instances of guide catheter "back out" during insertion or delivery of the support catheter. Guide catheters back out when a load is transmitted from a guidewire or device (e.g. support catheter, stent delivery system, PTCA balloon, etc.) to a guide catheter and the guide disengages from its preferred positioning, thereby decreasing guidewire support and creating the need for the medical professional to re-position the guiding catheter. To overcome problems associated with back out, many different support catheter tip shapes have been designed and deep seating techniques are used. These techniques are not without disadvantages, however, and may lead to vascular damage.

Additionally, many support catheters are ridged in order to prevent back out problems. However, such ridged support catheters can be traumatic to the patient's vasculature due to the rigidity being more susceptible to puncturing or otherwise damaging the inner surface of the vessel.

Certain procedures, such as valve replacements, valve repairs, and patent foramen ovale treatments in the heart, require that the treatment site be accessed by a guidewire that must pass from one side of heart to the other. After that is accomplished, a catheter device may be passed over the guidewire to access the treatment site on the second side of the heart. This requires that the guidewire pass through the septum, the wall of tissue that separates the right and left sides of a heart. The area of the septum that divides the two upper chambers is referred to as the atrial or interatrial septum and the area of the septum that divides the two lower chambers is referred to as the ventricular or interventricular septum. Puncturing the septum, however, is difficult and often leads to buckling of the guidewire.

Other procedures, such as treating arteries for disease often requires that a treatment site be accessed by a guidewire. For example, in the case of treating carotid arteries, the guidewire must travel from the aortic arch into the opening of the carotid artery (the carotid artery ostium). This passage may be complicated by the severity of the arch and the placement of the ostium. In the worst cases where difficult angles are present or other challenges exist, it may be extremely difficult to pass a guidewire. Even if guidewire access to the artery is established, it subsequently can be difficult to pass a treatment device into the artery because the difficult angles may prevent adequate support for delivery of the device, resulting in the guidewire falling out of position (or prolapse). Similar issues exist with the treatment of renal arteries, which can also be difficult to access because of the difficult angles in which they may come off the descending aorta.

It would be advantageous to have a support catheter that has the properties of flexibility and rigidity and at times when such properties are necessary. More particularly, it would be advantageous to have a support catheter that resists the temptation to backing out, buckling or prolapse under conditions where it would otherwise likely occur. In addition, it would be advantageous to have a support catheter that has these improved qualities for the purpose of puncturing a heart septum. Further, it would be advantageous to have a support catheter that has these improved qualities for the purpose of accessing difficult to reach arteries, e.g., accessing carotid or renal arteries from the aorta under difficult circumstances.

BRIEF SUMMARY OF THE INVENTION

To overcome the disadvantages with existing support catheters, disclosed is a support catheter having selective variable stiffness. In one configuration, the support catheter includes a catheter body having a proximal end, a distal end, and an interior wall surface defining a first lumen extending from the proximal end toward the distal end. A second lumen is disposed between the interior wall surface and an outer surface of the catheter body. A plurality of stiffening members is disposed around the second lumen, the plurality of stiffening members being engageable to selectively stiffen the catheter body. The second lumen may be adapted to receive fluid such that the support catheter can be stiffened by means of the fluid.

According to another configuration, the second lumen is defined by a first elastomeric member and a second elastomeric member spaced apart from the first elastomeric member. The movement of the elastomeric members aid with the engagement of the stiffening members to increase the catheter's stiffness. In another configuration, the catheter further comprises a second plurality of stiffening members disposed between the first lumen and the second lumen. The stiffening members can be disposed radially and/or axially.

In another configuration, the support catheter comprises a catheter body having a proximal end, a distal end, and an interior wall surface defining a first lumen extending from the proximal end toward the distal end. A second lumen is disposed between the interior wall surface and an outer surface of the catheter body, and a plurality of stiffening members is disposed between the first lumen and the second lumen.

The present invention has many applications. The following, which is not meant to be limiting, are some examples. The support catheter of the present invention can be used to treat a chronic total occlusion ("CTO"), i.e., recanalizing a CTO by for example, crossing the proximal cap of a CTO with a guidewire or other device, or exploiting the micro channels of a CTO. Also, the support catheter of the present invention can be used to treat carotid arteries because of the angles they may come off of the aortic arch, as well renal arteries, which also may be difficult to access because of the difficult angles in which they may come off the descending aorta. Further, the support catheter of the present invention is applicable where a medical professional needs to puncture a septum of a heart with a guidewire. Various procedures require this maneuver, such as valve replacements, valve repairs, and patent foramen ovale treatments.

Accordingly, the support catheter of the present invention also is applicable to patent foramen ovale ("PFO") treatments. A PFO is the term used for a heart septum that is not completely closed (particularly a flap or tunnel in the septum), and a PFO treatment contemplated herein is where a medical professional uses catheters and particularly a support catheter of the present invention to close the PFO. Yet further, the support catheter of the present invention also is applicable to annuloplasty valve repair. Annuloplasty is one way to do a mitral valve repair. A medical professional places a catheter around the annulus of the cardiac valve and then deploys anchors around the annulus so that the tension is exerted on the anchors to then close the mitral valve down. The support catheter of the present invention can be used in this procedure because can allow a medical professional to track along a guidewire into the annulus to stiffen it to deploy an anchor, and make it flexible again to retract the catheter to a different point, and then stiffen it again to deploy another anchor, and continue the same procedure for as many anchors as is necessary.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings.

DETAILED DESCRIPTION

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

As described herein, the support catheter is employed in placing a guidewire within a body lumen of a patient, such as, but not limited to, the lumen of a coronary artery. However, this description is exemplary only, and it should be appreciated that embodiments of the present catheter can be employed for multiple other purposes, including, but not limited to, the piercing of a blockage in a variety of body lumens, including the urinary tract, bile duct, esophagus and tracheo-bronchial tree, neurovascular, peripheral vascular, cardiac, and renal catheters, among others. Extra support is particularly beneficial during treatment of chronic total occlusions ("CTOs"), i.e., in recanalizing a CTO, crossing the proximal cap of CTO with a guidewire or other device or exploiting the micro channels of a CTO because the occlusion provides significant backload that is transmitted from the guidewire to the guide catheter that can lead to back out.

Generally, the present invention is related to support catheters. The support catheter can be configured so that a medical professional can position the support catheter through tortuous pathways while reducing the amount of guide catheter backup, buckling or prolapse of the catheter. In addition, and in particular, the support catheter of the present invention will allow for a medical professional to puncture a heart septum with a guidewire without buckling. Further, and in particular, the support catheter of the present invention will allow for a medical professional to access difficult to reach arteries such as carotid or renal arteries from the aorta under difficult circumstances. Further, as set forth above, the support catheter will benefit one performing PFO and annuloplasty.

Figure 1A:
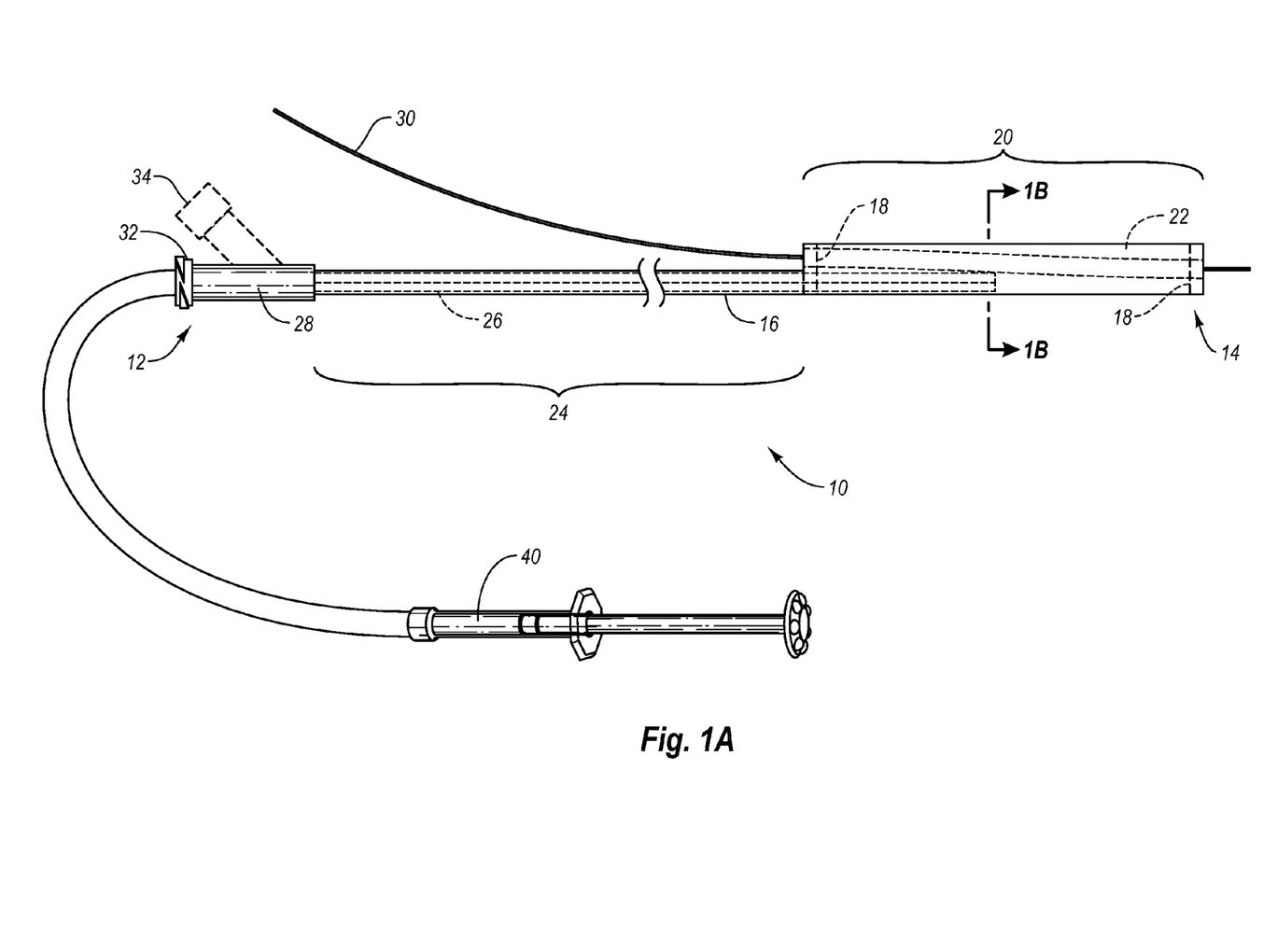
FIG. 1A illustrates a side view of an improved support catheter according to the present invention.

FIG. 1A illustrates a view of a catheter system that includes a support catheter 10 in fluid communication with an inflation device 40. The support catheter 10 functions or acts as a stiffening support catheter that can be used, from among other applications, to aid with puncturing a heart septum with a septal puncture needle, or to support a needle used to puncture the hepatic vein and hepatic portal vein and/or the liver as part of a Transjugular Intrahepatic Portosystemic Shunt, or "TIPS" procedure. In all of these cases and others, the support catheter 10 prevents backing out of the puncture needle or guidewire, promotes accurate puncture positioning and reduces the risk of perforation or puncture of adjacent bodily structures. One skilled in the art will readily appreciate the applicability of the present invention to any aspect of the aforementioned procedures as well as other procedures in which a stiffening support catheter 10 may be useful.

As shown, the support catheter 10 has a proximal end 12 and a distal end 14; the body of the catheter or catheter body 16 extends from the proximal end 12 toward the distal end 14. As illustrated, the support catheter 10 includes a distal portion 20, with a lumen 22 adapted to receive a structure 30 to be supported during a procedure, such as, but not limited to, a guidewire, a needle, or other flexible medical devices, that extends from the distal end 14 and terminates distal to the proximal end 12 of the catheter body 16. The support catheter 10 is thus illustrated in a rapid exchange configuration, however, it will be understood that the distal portion 20 can extend from the distal end 14 to the proximal end 12, and therefore function as over the wire support catheter. Also note that both ends of the distal portion 20 of the support catheter 10 contain radiopaque markers 18 so that they are visible under fluoroscopy, i.e., each end is marked with radiopaque material 18.

The support catheter 10 also includes a proximal portion 24 that acts as a fluid conduit with a portion of the distal portion 20. The proximal portion 24 includes a fluid lumen 26 that extends into a portion of the distal portion 20 and can provide a fluid, such as a liquid, gas, or combination thereof, to a portion of the distal portion 20.

Disposed at the proximal end 12 and/or proximal portion 24 is a port assembly 28 disposed at the proximal end 12. The port assembly 28 can optionally operate or function as a handle for a physician or clinician to manipulate the support catheter 10. In the illustrated configuration, the port assembly 28 includes a first port 32 usable to actuate or de-activate the support catheter 10 to decrease and/or increase the flexibility of the support catheter 10. For instance, the inflation device 40 can be coupled to the first port 32 to fluidly communicate with the support catheter 10. The inflation device 40 can be any of a variety of different inflation structures or systems, including but not limited to, fixed or movable powered or manually operated fluid injection systems or devices typically associated with the injection of a fluid into a medical device. As shown, the inflation device 40 has the form of a manually operated syringe, however, mechanically operated or other powered systems or devices are possible. The inflation device 40 can allow pressure or volume to control the introduction of fluid into the device 40. Exemplary inflation devices are produced by B. Braun, Merit Medical, and Cook, and typically have pressure ranges of 0 to 30 atm. It is contemplated that inflation pressures of approximately 10 atm are suitable for this invention, but this may be varied to reach different stiffness levels. Systems utilizing a canister of compressed gas, e.g., compressed $CO_2$, as long as it satisfies the required pressure ranges, also are possible. In general, a higher pressure will yield a stiffer catheter.

Optionally, and when the catheter 10 is configured as an over-the-wire catheter, the port assembly 28 can also includes a second port 34. In this configuration, the structure 30, such as a guidewire or other medical device can be placed and positioned through port 32 and port 34 is provided for the inflation device 40. It will be understood that the port assembly 28 can include additional ports as needed to accomplish the desired operation and usability of the support catheter 10.

Figure 1B:
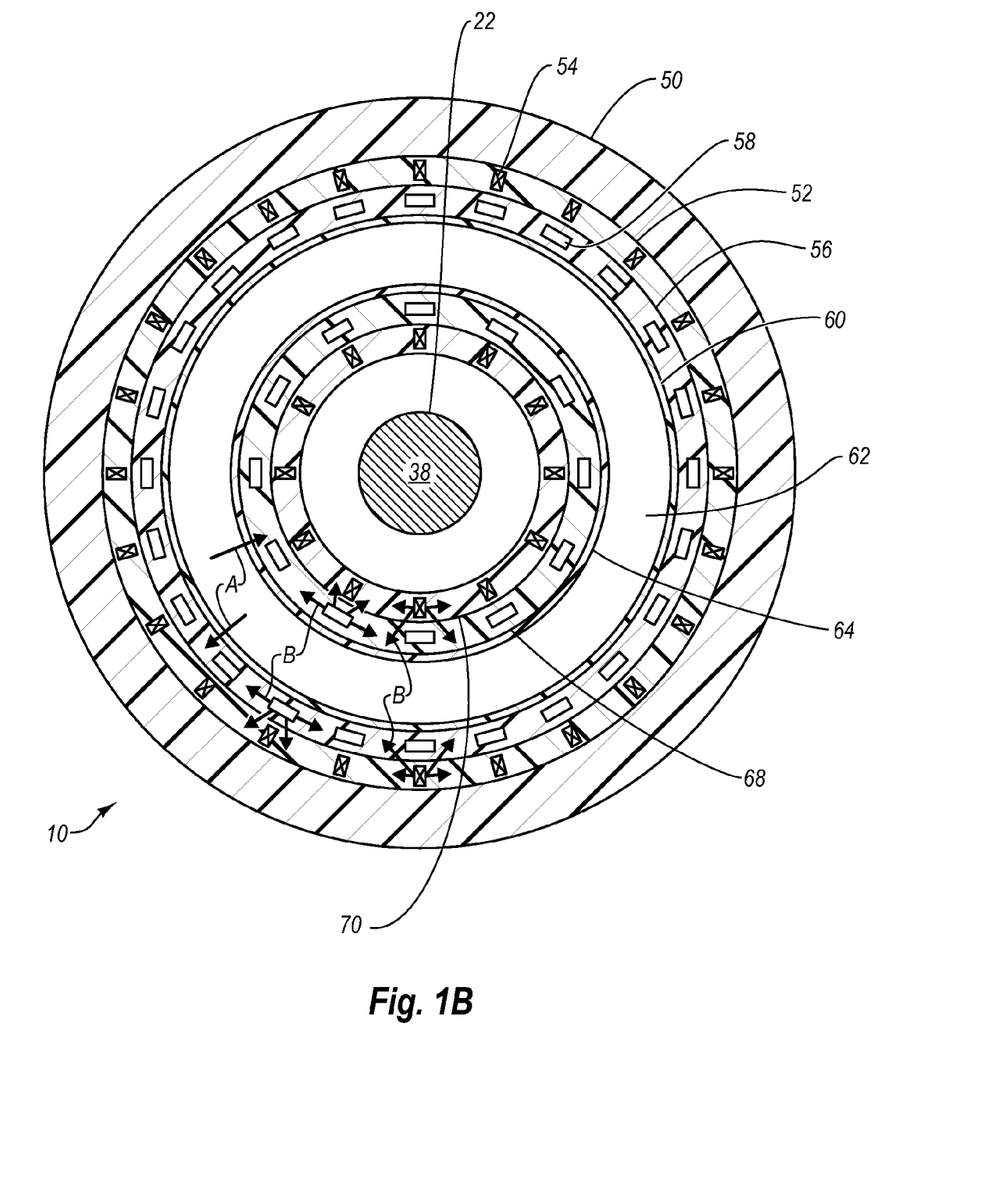
FIG. 1B illustrates a schematic cross-sectional view of the improved support catheter of FIG. 1.

Turning now to FIG. 1B, illustrated is a cross sectional view of the support catheter 10. As shown in cross-sectional view, the support catheter 10 includes an outer jacket layer 50 that defines an outer surface of the support catheter 10 and its catheter body. Disposed within the jacket layer 50, and forming the wall of the support catheter 10, are a first stiffening coil layer 52, a first stiffening band layer 56, an annular lumen 60 (or channel), a second stiffening band layer 68, and a second stiffening coil layer 70. The first stiffening coil layer 52 and the first stiffening band layer 56 can be considered, collectively, a first stiffening layer, while the second stiffening band layer 68 and the second stiffening coil layer 70 can be considered, collectively, as a second stiffening layer. It will be understood that although the illustrated embodiment includes both coil and band layers, each of the first and second stiffening layers can include only one of a coil or band layer, or both the first and second stiffening layers can be the same in that each can include either a coil or band layer.

Disposed within, and optionally defined by the interior wall surface of the second stiffening coil layer 70, is the lumen 22. This lumen 22 can receive the structure 30, such as a guidewire or other medical device during use of the support catheter 10.

Surrounding annular lumen 62, and optionally defining the annular lumen 62, is an outer wall 60 and an inner wall 64. The outer wall 60 and inner wall 64 are capable of flexing to enable the dimensions of the annular lumen 62 to change and thereby change the orientation and position of the layers 52, 56, 68, and 70 to change the stiffness of the support catheter 10. For instance, the outer wall 60 and inner wall 64 can be both made of an elastomeric material such as polyurethane, silicone or C-Flex®, the last of which can be manufactured by STI Components, Inc. of Morrisville, N.C., for example. More generally, the outer wall 60 and/or inner wall 64 can be fabricated from a polymeric material, a synthetic material, a natural material, or other material that provides the desired flexibility.

With continued reference to FIG. 1B, the outer jacket layer 50 defines the outer surface of the support catheter 10. As such, it may be desirable for the outer jacket layer 50, whether alone or in combination with another layer, to present a biocompatible surface to a body lumen within which it may be disposed. The outer jacket layer 50, therefore, can be made of a biocompatible material, such as a biocompatible polymeric material. Other suitable materials include polyimide, PEEK, polytetrafluorethylene, polyvinylidene fluoride, and polyamide. In addition, a biocompatible coating may be applied to any material that the catheter 10 may be composed of. For example, Heparin, which prevents blood clotting, may be used as such a biocompatible coating.

The first stiffening coil layer 52 and the second stiffening coil layer 70 of the support catheter 10 can be similar and can include one or more coiled wires 54, such as metallic or polymeric coils, positioned in radial directions. In contrast, the first stiffening band layer 56 and the second stiffening band layer 68 can be similar and can include one or more bands 58, such as metallic or polymeric bands, positioned in axial directions. Although reference is made to first and second coil and band layers, it will be understood that the first and second stiffening layers generally include one or more structures that cooperate together to change the stiffness of the support catheter 10, whether or not the sub-layers, i.e., first stiffening coil layer 52, first stiffening band layer 56, second stiffening coil layer 70, and second stiffening band layer 68, include coils, bands, ribbons, or other structures. Further, and more generally, the structures forming the stiffening coil layers and the stiffening band layers, whether individually, or collectively, can be considered as stiffening members.

Although larger ranges may work, stiffening layers could be formed from coiled wire with diameter 0.001 to 0.005 inch, and bands with thickness of 0.001 to 0.005 inch and width of 0.003 to 0.020 inch. Materials for the stiffening layers could include stainless steel, Nitinol, cobalt chrome, gold, platinum, eligloy, other metals, nylon, other polymers, and any combination thereof. Spacing between bands and coil turns can vary, but would likely be in the range of 0.003 to 2.0 inches, depending on the catheter location.

Further, within the spirit of the present invention, other embodiments of the supporting catheter 10 are contemplated. For example, instead of the axially aligned or radially-aligned coils or bands of the stiffening layers 52, 56, 68, and 70, such layers may be spirally-aligned or the layers may be any combination of any of the above. Also, the number or placement of stiffening layers may vary.

The support catheter 10 of the present invention overcomes the difficulties of existing support catheters through providing structures that enable a physician or clinician to vary the stiffness of the support catheter 10 as desired. Varying the quantity of fluid within the annular lumen 62 varies the stiffness of the support catheter 10. For instance, during a procedure using a guidewire as the structure 30, the guidewire 30 can be placed in position by itself. Then, at the location and time when the guidewire 30 needs stiffening, the remaining parts of the support catheter 10 are placed in position over the guidewire 30 by advancing it over the guidewire 30 until it reaches the desired location. Then, the annular lumen 62 is filled with a fluid by way of the fluid inflation device 40 (FIG. 1A) to inflate a portion of the catheter 10. With the aid of inflation device 40, an amount of fluid is infused into the lumen 62. In general, the inflation procedure is similar to the inflation step in a procedure that would be used by a physician performing a PTCA balloon angioplasty procedure.

When the annular lumen 62 inflates, the elastomeric walls 60 and 64 press against stiffening layers 52, 56, 68, and 70. Upon inflation, the elastomeric walls 60 and 64 move in the direction of arrows A, as shown in FIG. 1B. As each material and layer of the support catheter 10 presses against the stiffening layers 52, 56, 68, and 70, they move against each other and create friction or engage with each other so that they are prohibited from recovering to their original position. Specifically, as shown in FIG. 1B, the coiled wires 54 and the bands of wire 58 of the stiffening layers 52, 56, 68, and 70 will shift in various directions, as represented by arrows B. By doing so, the coiled wires 54 and the bands of wires 58 will intermesh with each other at adjacent layers as well as within each layer. More specifically, inflation imparts forces on layers 56 and 68 such that bands of wires 58 in layers 56 and 68 move in various directions B and particularly into adjacent layers 56 and 68. In response to these forces, the coiled wires 54 move in various directions B into and particularly into adjacent layers 52 and 70. This intermeshing process is aided by the elastomeric material of walls 60 and 64 that forces its way into the gaps of any stiffening layers 52, 56, 68, and 70. Thus, the stiffening layers 52, 56, 68, and 70 become locked in their new positions, optionally even after the annular lumen 62 is deflated. Therefore, after deflation of the annular lumen 62, there is sufficient flexibility of the catheter 10 for the physician or clinician to use the guidewire 30, when such is the structure, to advance any treatment devices over guidewire 30. In other configurations of the support catheter 10, however, the stiffening layers 52, 56, 68, and 70 may optionally return to their original positions after the annular lumen 62 is deflated. In this way, the support catheter 10 may be removed from a treatment site more easily and with less chance of bodily injury than if the annular lumen 62 had not been deflated prior to removal. To facilitate maintaining pressure in the catheter 10, a valve may be disposed on the port assembly 28 such that the inflation device 40 may be decoupled from the support catheter 10 and removed.

Figure 2:
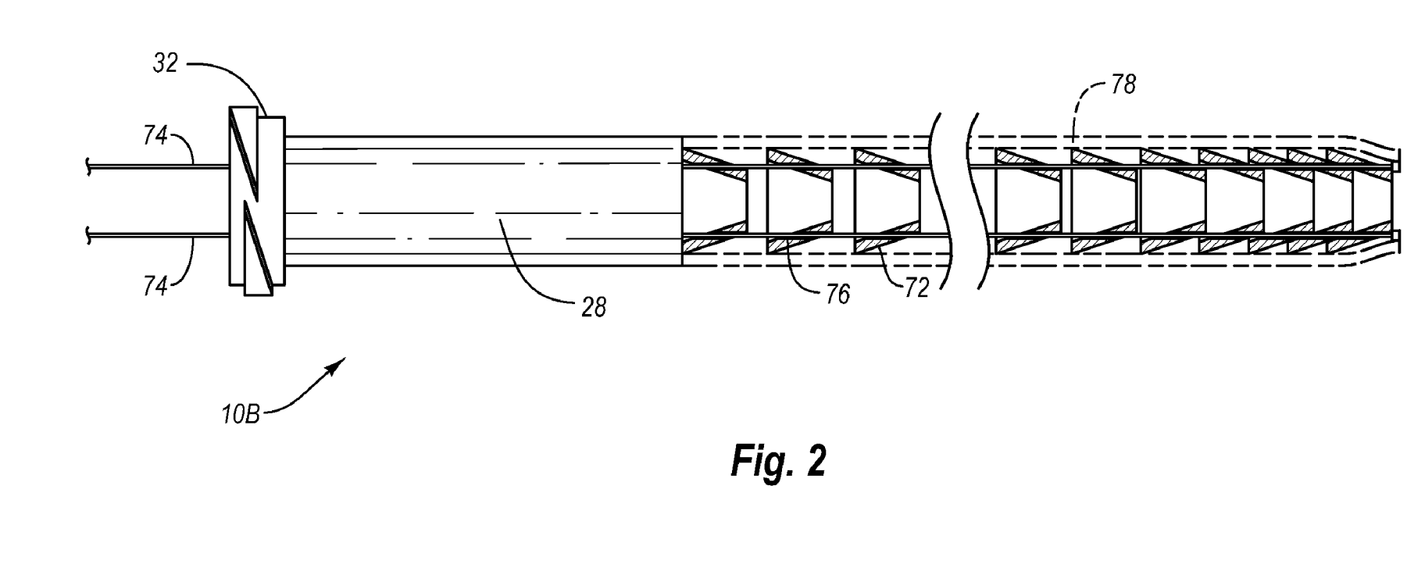
FIG. 2 shows a partial cross-sectional side view of an alternate embodiment of a support catheter according to the present invention.

FIG. 2 shows a partial cross-sectional side view of an alternate embodiment of a support catheter 10B according to the present invention. Support catheter 10B comprises a plurality of conically-shaped members or truncated cones 72 that are movably linked by two cables 74, which pass through holes or respective passageways 76 in each conically-shaped member 72. The plurality of conically-shaped members 72 are situated on the port assembly 28, which contains a first port 32, out of which emanate the two cables 74.

The truncated cones 72 are generally concentric in that they fit inside one another, as shown in FIG. 2. When the two cables 74 are pulled from the first port 32, the truncated cones 72 are forced closer together, and in turn, the arrangement and thereby the support catheter 10B becomes stiffer. Accordingly, in practice, the alignment of truncated cones 72 is used as a support catheter 10B just as support catheter 10 can be used as described above. The cables 74 can be any thin elongated material suitable for working inside the body, such as wire, line, cord, or the like.

Once a structure 30, such as a guidewire, needle, or other medical device, is in position, the catheter 10B can be advanced over the structure 30. The relative stiffness of the support catheter 10B can be adjusted by the medical professional by means of the cables 74. Note that although two cables 74 are shown in the embodiment of FIG. 2, only one cable 74 is necessary and more than two cables 74 may be utilized. Also note that the truncated cones 72 of support catheter 10B of FIG. 2 are shown in various modes of alignment. That is, those truncated cones 72 on the distal end of catheter 10B are shown in relatively tight engagement, whereas those shown on the proximal end of the catheter 10B are shown separated from each other for illustrative purposes. Accordingly, in practice, as understood by one skilled in the art, the truncated cones 72 would be aligned similar to those shown on the distal end of catheter 10B, as friction between the truncated cones 72 and the cables 74 holds the catheter 10B together and allows it to both advance over the structure 30, but also to provide support to the structure 30. The truncated cones 72 may also have modified surfaces to increase the friction therebetween. That is, they may be coated with a material having a higher friction than the core, such as silicone, or they may be roughened or knurled to increase friction.

The truncated cones 72 of catheter 10B may be manufactured from any number of materials. For example, such suitable materials may include metals, metal alloys, polymers, synthetic materials, natural materials, combinations thereof, or other materials that provide the desired stiffness and/or biocompatibility. Suitable metals include stainless steel, Nitinol, eligloy, and cobalt chromium. Suitable polymers include PTFE, ePTFE, PEEK, polyimide, and Pebax. Further, catheter 10B may further comprise an outer jacket layer 78, as shown in phantom lines in FIG. 2. The outer jacket layer 78 may be made of a biocompatible material, such as a biocompatible polymeric material. Suitable biocompatible polymeric materials for the outer jacket layer 78 may include polyimide, PEEK, polytetrafluorethylene, polyvinylidene fluoride, and polyamide, although other materials are possible.

Figure 3A:
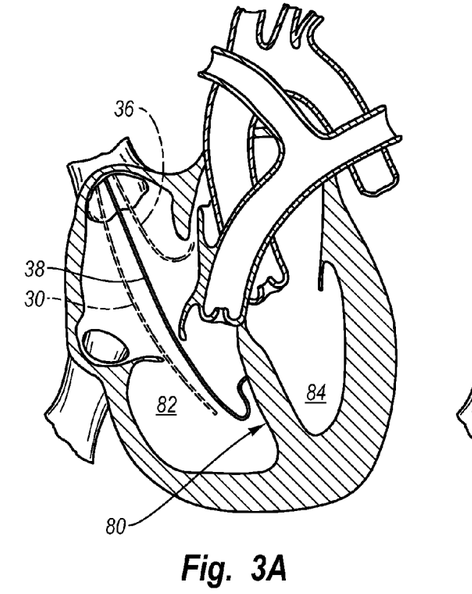
FIG. 3A illustrates a schematic view of an attempt at puncturing of a heart septum with a lone guidewire.

FIG. 3A shows a schematic view of an attempt at puncturing a heart septum 80, i.e., the wall of tissue that separates one side 82 from the other side 84 of a heart that can benefit from using the catheter of the present invention. The following discussion will be directed to advancing a needle 38 as the structure supported by the catheter 10 through the septum 80. The septum 80 is relatively substantial tissue. Thus, as shown in FIG. 3A, when the puncture is attempted with only a needle 38, the needle 38 buckles.

Figure 3B:
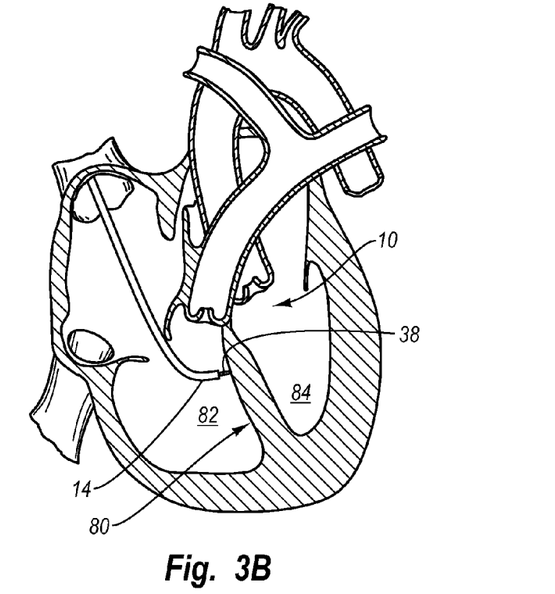
FIG. 3B illustrates a schematic view of the catheter of FIG. 1A in cooperation with a guidewire, advanced over the guidewire, wherein the catheter is in a flexible state.
Figure 3C:
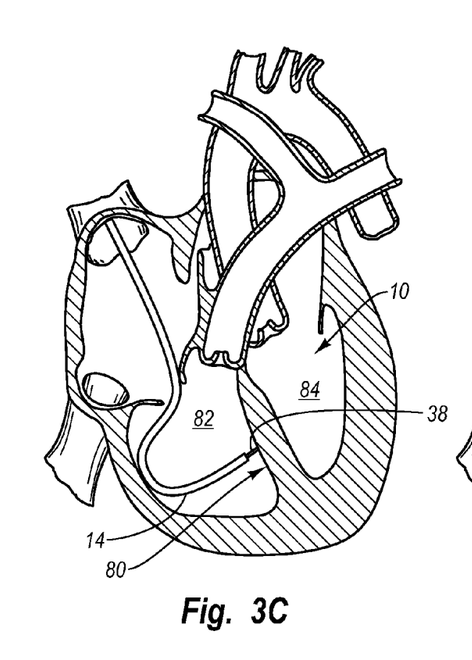
FIG. 3C illustrates a schematic view of the catheter of FIG. 1A in cooperation with the guidewire of FIG. 3B, advanced over the guidewire, wherein the catheter is in a stiffened state.

FIG. 3B shows a schematic view of the catheter 10 in cooperation with the needle 38. To prevent buckling, the needle 38 is first positioned to the point where the distal end reaches the desired destination. In this case, the desired location is where the needle 38 abuts the septum 80. At this point, the catheter 10 is advanced over the needle 38 until the catheter 10 reaches almost the same point, i.e., almost to the septum 80, and situated against resting points within the heart, as shown in the schematic view of FIG. 3C. Stated another way, the catheter 10 is advanced along the needle 38 until the distal end 14 is proximal to the distal end of the needle 38.

When the catheter 10 is positioned, the catheter 10 is then actuated or stiffened. That is, and with reference to FIGS. 1A and 1B, fluid is passed along the lumen 26 to the annular lumen 62 to inflate a portion of the distal portion 20. With the fluid inflating the distal portion 20, the stiffening layers 52, 56, 68, and 70 engage and stiffen the catheter 10. Accordingly, with the support catheter 10 providing support to the needle 38, and particularly situated against the rest points within the heart, the catheter 10 prevents any buckling and reduces any backlash of the needle 38.

Figure 3D:
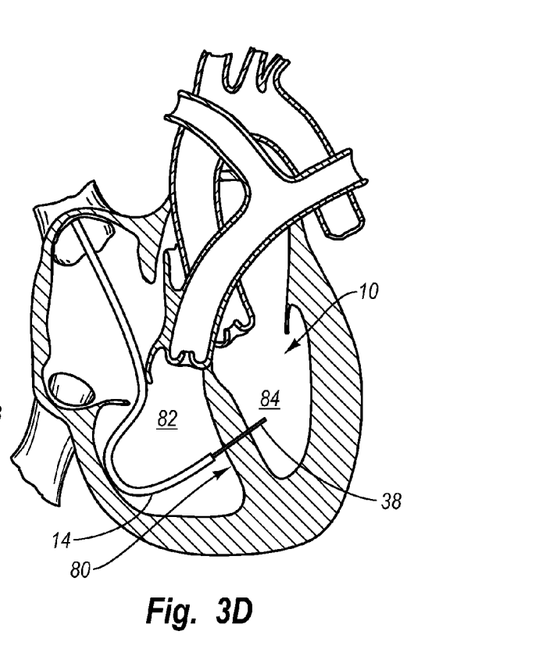
FIG. 3D illustrates a schematic view of puncturing a heart septum with the guidewire of FIG. 3B after the catheter of FIG. 3B has been actuated and removed.

Thus, as shown in the schematic view of FIG. 3D, the needle 38, and optionally the catheter 10, can be advanced within the catheter 10 and into the second side 84 of the heart. After the needle 38 reaches its intended destination on the second side 84, i.e., the treatment site, the support catheter 10 can then be deflated by removing fluid from the annular lumen 62 and removed over the needle 38. Lastly, with the distal end of the needle 38 in place on the second side 84 of the septum 80, any treatment devices can be positioned in place by being advanced over the needle 38.

In those circumstances when the catheter 10 is not advanced through the septum 80, the guidewire 30 can be supported by the catheter 10 as it is advanced through the puncture formed by the needle 38. Alternatively, the guidewire 30 can be supported by the catheter 10 in those instances when the guidewire 30 can be used to puncture tissue. In still other configurations, the catheter 10 can support a guidewire, such as guidewire 36 shown in phantom, as part of treatment of a patent foramen ovale ("PFO"). Generally, the catheter 10 can be used to support any structure for which it may be possible to reduce backlash or back up of the structure.

Figure 4A:
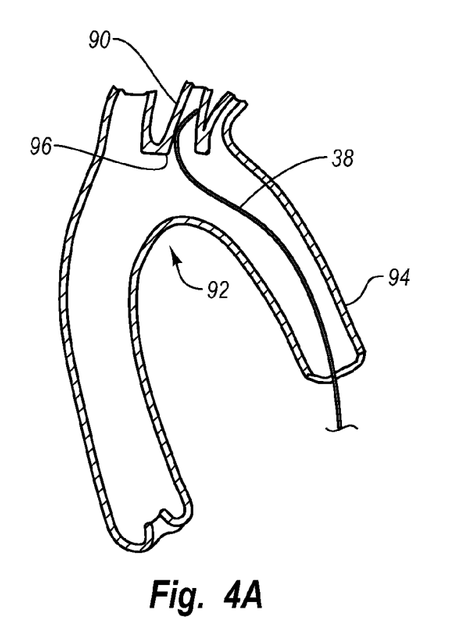
FIG. 4A shows a schematic view of an attempt at accessing a carotid artery from an aortic arch.
Figure 4B:
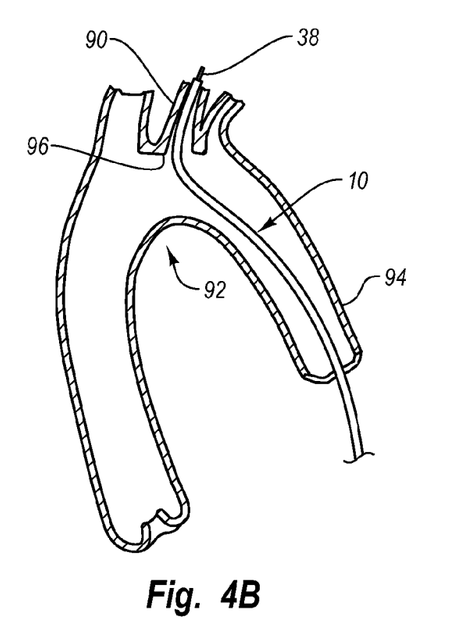
FIG. 4B shows a schematic view of a catheter in cooperation with a guidewire, advanced over the guidewire, wherein the catheter is in a flexible state.
Figure 4C:
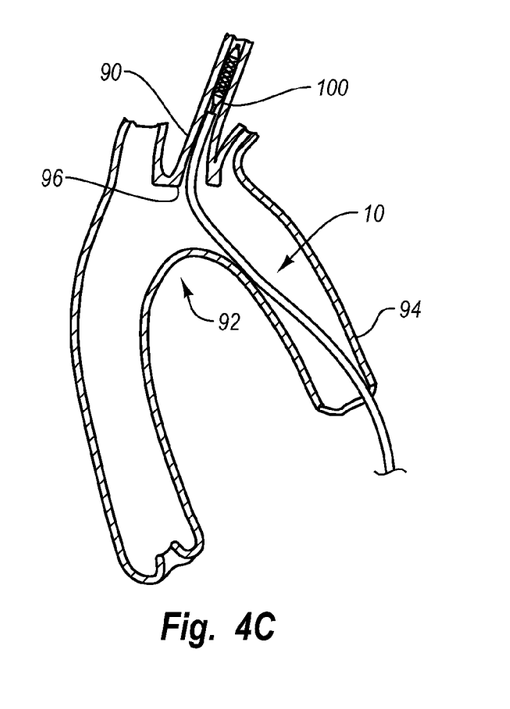
FIG. 4C shows a schematic view of the catheter of FIG. 4B in its inflated state, advanced over a guidewire, wherein the guidewire has a treatment device on its distal end.

FIGS. 4A-4C shows a schematic view of the catheter 10 being used to access a carotid artery 90 from an aortic arch 92. As shown, the guidewire 30 enters from the descending aorta 94 and enters the carotid artery ostium 96, which may be difficult to navigate. As set forth above, even if the guidewire 30 may be able to access the ostium 96, navigating the remainder of the carotid artery 90 may be difficult, or it subsequently can be difficult to pass a treatment device into the artery 90 because the difficult angles may prevent adequate support for delivery of the device, resulting in the guidewire 30 falling out of position, i.e., guidewire prolapse. Thus, support for the guidewire 30 is desirable.

To prevent guidewire prolapse or to allow for proper advancement of a guidewire 30 or proper delivery of a treatment device, the guidewire 30 is first positioned to the point where the distal end reaches the desired destination such as shown in FIG. 4A. The desired location is at the opening of the target vessel, or more preferably, just past the opening of the target vessel, i.e., in this case, where the guidewire 30 has just passed the carotid artery ostium 96.

FIG. 4B shows a schematic view of the catheter 10 in cooperation with the guidewire 30. At this point, the catheter 10 is advanced over the guidewire 30 until the catheter 10 reaches almost the same point in the target vessel. This advancement of the support catheter 10 is made easier because the support catheter is still in its flexible state during tracking. After advancement of the catheter 10, it is then actuated or stiffened. That is, the annular lumen 62 (FIG. 1B) is then inflated as described above.

FIG. 4C shows a schematic view of the stiffening catheter 10 in its inflated state. Once inflated, the catheter 10 assumes the shape that it was in prior to inflation. With the stiffening catheter 10 providing support to the guidewire 30, the catheter 10 and disclosed method prevents any prolapse and allows for proper advancement of the guidewire 30 and proper delivery of a treatment device. As noted above, renal arteries have similarly difficult access angles. Accordingly, this invention has applicability there as well.

In the inflated configuration, a treatment device 100, such as a balloon catheter, stent delivery system, embolic protection device, ultrasonic diagnostic device, atherectomy device such as a rotoblator or other plaque removal device can be advanced through the catheter 10, over the guidewire 30, extended out of the distal end of the support catheter 10 and into the carotid artery 90 or other target location, as shown in FIG. 4C. Alternatively, the guidewire 30 may be replaced with a guidewire having a different stiffness. Further, with the added support provided by the stiffening catheter 10, the guidewire 30 may be advanced more directly into a vessel, i.e., to a treatment site farther into the carotid artery 90 without contacting or damaging walls of the carotid artery 90.

Other catheters may be used to accomplish the same result as catheter 10. That is, if a catheter provides support to the guidewire 30 it may be used with the same method for puncturing a septum 80 or accessing difficult to reach arteries as the methods described herein with catheter 10. For example, as set forth above, different variations of the stiffening support catheter 10 are possible.

The present invention provides a stiffening support catheter 10 than can provide support to a guidewire 30 so that it may puncture a heart septum 80 or access difficult to reach arteries in order to access a treatment site, and methods for utilizing the same. In doing so, the present invention discloses an improved stiffening support catheter 10 that can be used in other applications where a support catheter is needed or helpful. Lastly, it is important to bear in mind that the stiffening support catheter of the present invention changes between a flexible and a stiffened state.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed is:

1. A support catheter comprising:
a catheter body having selectively variable stiffness, the catheter body having a proximal end, a distal end, and an interior wall surface defining a first lumen extending from the proximal end toward the distal end;
a second lumen disposed between the interior wall surface and an outer surface of the catheter body; and
a plurality of stiffening members disposed between the first lumen and the second lumen, the catheter body having a first flexible state in which the plurality of stiffening members are in a first unengaged, non-intermeshed, non-stiffening state and the catheter body having a second stiffened state in which the plurality of stiffening members are in a second engaged, stiffening state wherein the plurality of stiffening members in the second engaged, stiffening state intermesh with one another to selectively stiffen the catheter body.

2. The support catheter as recited in claim 1, further comprising a port assembly disposed at the proximal end.

3. The support catheter as recited in claim 1, further comprising a first elastomeric member and a second elastomeric member spaced apart from the first elastomeric member, the first and second elastomeric members defining the second lumen.

4. The support catheter as recited in claim 1, wherein at least one of the plurality of stiffening members comprises a radially orientated stiffening member and at least one of the plurality of stiffening members comprises an axially orientated stiffening member.

5. The support catheter as recited in claim 4, wherein the radially orientated stiffening member comprises a stiffening band or stiffening coil and the axially orientated stiffening member comprises a stiffening band or stiffening coil.

6. The support catheter as recited in claim 1, wherein the second lumen is adapted to receive fluid such that the support catheter can be inflated by means of the fluid.

7. A support catheter comprising:
a catheter body having selectively variable stiffness, the catheter body having a proximal end, a distal end, and an interior wall surface defining a first lumen extending from the proximal end toward the distal end;
a second lumen disposed between the interior wall surface and an outer surface of the catheter body;
a first plurality of stiffening members disposed between the first lumen and the second lumen, the first plurality of stiffening members having a first unengaged, non-intermeshed, non-stiffening state and a second engaged, stiffening state wherein the first plurality of stiffening members in the second state intermesh with one another to selectively stiffen the catheter body;
a second plurality of stiffening members disposed around the second lumen, the second plurality of stiffening members having a first unengaged, non-intermeshed, non-stiffening state and a second engaged, stiffening state wherein the second plurality of stiffening members in the second engaged, stiffening state intermesh with one another to selectively stiffen the catheter body,
wherein the catheter body has a first flexible state when the first and second pluralities of stiffening members are in the first unengaged, non-intermeshed, non-stiffening state and the catheter body has a second stiffened state when at least one of the first or second pluralities of stiffening members are in the second engaged, stiffening state, and
wherein at least one of the first plurality of stiffening members or the second plurality of stiffening members is adapted to transition to a third unengaged, non-intermeshed, non-stiffening state where the catheter body has a third flexible state after formation of the second engaged, stiffening state.

8. The support catheter as recited in claim 7, further comprising a first elastomeric member and a second elastomeric member spaced apart from the first elastomeric member, the first and second elastomeric members defining the second lumen.

9. The support catheter as recited in claim 7, wherein at least one of the first plurality of stiffening members comprises a radially orientated stiffening member and at least one of the first plurality of stiffening members comprises an axially orientated stiffening member.

10. The support catheter as recited in claim 9, wherein the radially orientated stiffening member comprises a stiffening band or stiffening coil and the axially orientated stiffening member comprises a stiffening band or stiffening coil.

11. The support catheter as recited in claim 7, wherein at least one of the second plurality of stiffening members comprises a radially orientated stiffening member and at least one of the second plurality of stiffening members comprises an axially orientated stiffening member.

12. The support catheter as recited in claim 11, wherein the radially orientated stiffening member comprises a stiffening band or stiffening coil and the axially orientated stiffening member comprises a stiffening band or stiffening coil.

13. The support catheter as recited in claim 1, wherein at least a portion of the plurality of stiffening members is adapted to transition to a third unengaged, non-intermeshed, non-stiffening state after formation of the second engaged, stiffening state.

14. The support catheter as recited in claim 13, wherein the third unengaged, non-intermeshed, non-stiffening state is the same as the first unengaged, non-intermeshed, non-stiffening state.

15. The support catheter as recited in claim 13, wherein the third unengaged, non-intermeshed, non-stiffening state is the same as the first unengaged, non-intermeshed, non-stiffening state.

16. The support catheter as recited in claim 7, wherein the third unengaged, non-intermeshed, non-stiffening state is the same as the first unengaged, non-intermeshed, non-stiffening state.

17. The support catheter as recited in claim 7, wherein the third unengaged, non-intermeshed, non-stiffening state is the same as the first unengaged, non-intermeshed, non-stiffening state.

18. A support catheter comprising:
a catheter body having selectively variable stiffness, the catheter body having a proximal end, a distal end, and an interior wall surface defining a first lumen extending from the proximal end toward the distal end;
a second lumen disposed between the interior wall surface and an outer surface of the catheter body; and
a plurality of stiffening members disposed between the first lumen and the second lumen, the catheter body having a first flexible state in which the plurality of stiffening members are in a first unengaged, non-stiffening state wherein the plurality of stiffening members are substantially non-intermeshed with one another and the catheter body having a second stiffened state in which the plurality of stiffening members are in a second engaged, stiffening state wherein the plurality of stiffening members in the second engaged, stiffening state intermesh with one another to selectively stiffen the catheter body.

19. The support catheter as recited in claim 18, further comprising a port assembly disposed at the proximal end.

20. The support catheter as recited in claim 18, further comprising a first elastomeric member and a second elastomeric member spaced apart from the first elastomeric member, the first and second elastomeric members defining the second lumen.

21. The support catheter as recited in claim 18, wherein at least one of the plurality of stiffening members comprises a radially orientated stiffening member and at least one of the plurality of stiffening members comprises an axially orientated stiffening member.

22. The support catheter as recited in claim 21, wherein the radially orientated stiffening member comprises a stiffening band or stiffening coil and the axially orientated stiffening member comprises a stiffening band or stiffening coil.

23. The support catheter as recited in claim 18, wherein the second lumen is adapted to receive fluid such that the support catheter can be inflated by means of the fluid.

24. The support catheter as recited in claim 18, wherein at least a portion of the plurality of stiffening members is adapted to transition to a third unengaged, non-intermeshed, non-stiffening state after formation of the second engaged, stiffening state.

25. The support catheter as recited in claim 24, wherein the third unengaged, non-intermeshed, non-stiffening state is the same as the first unengaged, non-intermeshed, non-stiffening state.

26. The support catheter as recited in claim 24, wherein the third unengaged, non-intermeshed, non-stiffening state is the same as the first unengaged, non-intermeshed, non-stiffening state.

* * * * *